(12) United States Patent
Copeland et al.

(10) Patent No.: US 11,141,099 B2
(45) Date of Patent: Oct. 12, 2021

(54) REMOTE DELIVERY AND MONITORING OF HEALTH CARE

(71) Applicant: INTERNATIONAL BUSINESS MACHINES CORPORATION, Armonk, NY (US)

(72) Inventors: Michael P. Copeland, Vail, AZ (US); Mark S. Fleming, Oro Valley, AZ (US); Christina A. Lara, Tucson, AZ (US); Calline K. Sanchez, Tucson, AZ (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1192 days.

(21) Appl. No.: 14/866,517

(22) Filed: Sep. 25, 2015

(65) Prior Publication Data
US 2016/0007920 A1    Jan. 14, 2016

Related U.S. Application Data

(62) Division of application No. 12/409,779, filed on Mar. 24, 2009, now Pat. No. 9,844,333.

(51) Int. Cl.
*A61B 5/00* (2006.01)
*G16H 30/40* (2018.01)
(Continued)

(52) U.S. Cl.
CPC ............ *A61B 5/445* (2013.01); *A61B 5/0013* (2013.01); *A61B 5/0022* (2013.01);
(Continued)

(58) Field of Classification Search
CPC .... H02J 7/0004; A61B 8/4227; A61B 8/4281; A61B 2017/2253; A61B 2560/0475;
(Continued)

(56) References Cited

U.S. PATENT DOCUMENTS

| 4,498,467 A | | 2/1985 | Kirkpatrick et al. |
| 4,649,933 A | * | 3/1987 | Jackson ............... A61F 13/041 600/587 |

(Continued)

FOREIGN PATENT DOCUMENTS

| DE | 2944726 A1 | 6/1981 |
| EP | 0278631 | 1/1988 |

(Continued)

OTHER PUBLICATIONS

Lim et al., "A Novel Image Capture System for Use in Telehealth Applications" pp. 4743-4746, Proceedings of the 28th IEEE EMBS Annual International Conference, New York City, Aug. 30-Sep. 3, 2006.

(Continued)

*Primary Examiner* — Keith M Raymond
*Assistant Examiner* — Helene Bor
(74) *Attorney, Agent, or Firm* — Griffiths & Seaton PLLC

(57) ABSTRACT

Various embodiments for providing remote delivery and monitoring of health care are provided. In one embodiment, a portable apparatus for orthopedic monitoring of a patient is provided and comprises: a housing adapted for one of positioning adjacent to and positioning within an orthopedic cast; a diagnostic biomedical device integrated into the housing, wherein the diagnostic biomedical device is adapted for obtaining an orthopedic image of a portion of the patient treated with the orthopedic cast; and a wireless communications interface coupled to the diagnostic biomedical device, wherein the wireless communications interface is adapted to upload the orthopedic image to a remote server to be viewed by a medical professional.

4 Claims, 12 Drawing Sheets

(51) Int. Cl.
*G16H 40/67* (2018.01)
*A61B 10/00* (2006.01)
*A61B 90/00* (2016.01)

(52) U.S. Cl.
CPC .......... *A61B 5/0059* (2013.01); *A61B 5/6812* (2013.01); *A61B 5/7207* (2013.01); *A61B 5/74* (2013.01); *A61B 5/7445* (2013.01); *G16H 30/40* (2018.01); *G16H 40/67* (2018.01); *A61B 10/0045* (2013.01); *A61B 2090/376* (2016.02); *A61B 2090/378* (2016.02); *A61B 2560/0214* (2013.01); *A61B 2560/0431* (2013.01); *A61B 2560/0456* (2013.01); *A61B 2560/0475* (2013.01)

(58) Field of Classification Search
CPC .... A61B 2560/0456; A61B 2560/0431; A61B 2560/0214; A61B 10/0045; A61B 2090/378; A61B 5/445; A61B 5/0013; A61B 2090/376; A61B 5/0022; A61B 5/0059; A61B 5/6812; A61B 5/7207; A61B 5/74; A61B 5/7445; A61N 7/00; B06B 1/0246; G16H 40/67; G06F 19/3418

See application file for complete search history.

(56) References Cited

U.S. PATENT DOCUMENTS

| | | | |
|---|---|---|---|
| 4,688,580 A * | 8/1987 | Ko | A61B 5/053 600/547 |
| 4,860,756 A | 8/1989 | Ko et al. | |
| 5,626,151 A | 5/1997 | Linden | |
| 5,792,076 A | 8/1998 | Orsak et al. | |
| 5,975,081 A | 11/1999 | Hood et al. | |
| 6,034,296 A | 3/2000 | Elvin et al. | |
| 6,112,224 A | 8/2000 | Peifer et al. | |
| 6,213,958 B1 * | 4/2001 | Winder | A61B 5/6843 600/442 |
| 6,261,249 B1 * | 7/2001 | Talish | A61B 8/4227 600/459 |
| 6,393,431 B1 | 5/2002 | Salvati et al. | |
| 6,409,661 B1 | 6/2002 | Murphy | |
| 6,603,552 B1 | 8/2003 | Cline et al. | |
| 6,641,532 B2 | 11/2003 | Iliff | |
| 6,652,461 B1 * | 11/2003 | Levkovitz | A61B 8/04 128/916 |
| 6,692,436 B1 | 2/2004 | Bluth et al. | |
| 7,122,005 B2 | 10/2006 | Shusterman | |
| 7,167,244 B2 | 1/2007 | Mullani | |
| 7,232,220 B2 | 6/2007 | Franz et al. | |
| 7,314,457 B2 | 1/2008 | Reaux | |
| 7,384,146 B2 | 6/2008 | Covannon et al. | |
| 7,359,748 B1 | 8/2008 | Drugge | |
| 7,412,396 B1 | 8/2008 | Haq | |
| 7,685,005 B2 | 3/2010 | Riff et al. | |
| 7,766,365 B2 | 8/2010 | Darling, III | |
| 2001/0025226 A1 | 9/2001 | Lavery | |
| 2001/0037070 A1 | 11/2001 | Cranley et al. | |
| 2001/0056226 A1 | 12/2001 | Zodnik et al. | |
| 2002/0115916 A1 | 8/2002 | Sjoqvist | |
| 2003/0146977 A1 * | 8/2003 | Vale | H04N 1/00488 348/207.1 |
| 2004/0019406 A1 | 1/2004 | Wang et al. | |
| 2004/0044560 A1 | 3/2004 | Giglio et al. | |
| 2005/0097173 A1 | 5/2005 | Johns et al. | |
| 2005/0101884 A1 | 5/2005 | Weeks et al. | |
| 2005/0131493 A1 | 6/2005 | Boveja et al. | |
| 2005/0201205 A1 * | 9/2005 | Chavez | G10K 11/02 367/152 |
| 2005/0212912 A1 | 9/2005 | Huster | |
| 2005/0277872 A1 | 12/2005 | Colby et al. | |
| 2006/0101727 A1 | 5/2006 | Holgerson et al. | |
| 2006/0111620 A1 | 5/2006 | Squilla et al. | |
| 2006/0271409 A1 | 11/2006 | Rosenfeld et al. | |
| 2007/0073113 A1 | 3/2007 | Squilla et al. | |
| 2007/0129610 A1 | 6/2007 | Squilla | |
| 2007/0225578 A1 | 9/2007 | Howell et al. | |
| 2007/0255115 A1 | 11/2007 | Anglin et al. | |
| 2007/0255155 A1 | 11/2007 | Anglin, Jr. et al. | |
| 2007/0293912 A1 * | 12/2007 | Cowan | A61N 1/326 607/51 |
| 2007/0299316 A1 | 12/2007 | Haslehurst et al. | |
| 2008/0068447 A1 | 3/2008 | Mattila et al. | |
| 2008/0076973 A1 | 3/2008 | Muradia | |
| 2008/0119958 A1 | 5/2008 | Bear et al. | |
| 2008/0194928 A1 | 8/2008 | Mandie et al. | |
| 2008/0262347 A1 * | 10/2008 | Batchelder | A61B 5/6828 600/437 |
| 2008/0264708 A1 | 10/2008 | Grange et al. | |
| 2008/0292151 A1 | 11/2008 | Kurtz et al. | |
| 2009/0036780 A1 * | 2/2009 | Abraham | A61B 8/08 600/459 |
| 2009/0063187 A1 | 3/2009 | Johnson et al. | |
| 2009/0112621 A1 | 4/2009 | Jung et al. | |
| 2009/0231125 A1 | 9/2009 | Baldus et al. | |
| 2009/0234672 A1 | 9/2009 | Dicks et al. | |
| 2009/0240115 A1 | 9/2009 | Bluth | |
| 2009/0240524 A1 | 9/2009 | Bluth | |
| 2009/0240527 A1 | 9/2009 | Bluth | |
| 2009/0264712 A1 | 10/2009 | Baldus et al. | |
| 2010/0185711 A1 | 7/2010 | Subramaniam | |
| 2011/0213620 A1 | 9/2011 | Dziubinski | |
| 2011/0213625 A1 | 9/2011 | Joao | |
| 2011/0282212 A1 * | 11/2011 | Hyoun | A61B 8/00 600/459 |
| 2012/0218123 A1 * | 8/2012 | Ji | A61B 5/7232 340/870.07 |
| 2013/0242262 A1 | 9/2013 | Lewis | |
| 2015/0305619 A1 | 10/2015 | Liang | |

FOREIGN PATENT DOCUMENTS

| | | |
|---|---|---|
| JP | 9021155 | 1/1997 |
| WO | 2007090543 A1 | 8/2007 |
| WO | 2008064120 A2 | 5/2008 |

OTHER PUBLICATIONS

"A portable battery operated bone fracture evaluator" Proceedings—19th International Conference—IEEE/EMBS Oct. 30-Nov. 2, 1997 Chicago, IL, USA.

Vander Haeghen et al., "An Imaging System with Calibrated Color Image Acquisition for Use in Dematology" pp. 772-730, vol. 19, No. 7, Jul. 2000.

Maar, "Doctor as Inventor and Visionary: Dr. Rhett Drugge, Dermatologist, Fights Skin Cancer with Sophisticated New Invention" http://www.thebestdermatologist.com/derm/news.html, printed on Mar. 9, 2009.

Komiya et al., "Natural Color Reproduction System for Telemedicine and Its' Application to Digital Camera" IEEE, 1999, pp. 50-54 vol. 3.

Ohya, "Natural Color Reproduction System for Telemedicine" pp. 442-449, IEEE, 1998.

Kiebzak, "Radiolucent casting tape allows for accurate measurement of forearm bone mineral density using dual energy X-ray absorptiometry" Miller Orthopedic Clinic, Charlotte, NC, PMID: 1534883 [PubMed], 1998.

Heying, Philip, "City rolls out solar panels on ambulance in order to save a few bucks", Mar. 4, 2009, 2 pages, LJWorld.com.

Abel, Jonathan, "Sunstar ambulances tap the sun to tack on power", Dec. 17, 2008, 1 page, Tampa Bay Times, Tampa Bay, FL, USA.

English Translation of DE2944726, Hager Reinhard Klaus Ing, Jun. 4, 1981 (7 pages).

* cited by examiner

REMOTE DELIVERY AND MONITORING OF HEALTH CARE

CROSS-REFERENCE TO RELATED APPLICATIONS

This Application is a Divisional Application of U.S. patent application Ser. No. 12/409,779, filed on Mar. 24, 2009, the contents of which are incorporated herein by reference.

BACKGROUND OF THE INVENTION

Field of the Invention

The present invention relates in general to computers and computer-assisted devices, and more particularly to apparatus, method and computer program product embodiments of devices for providing medical care with the remote assistance of a medical professional.

Description of the Related Art

Computers and computer systems are found in a variety of settings in today's society. Computing environments and networks may be found at home, at work, at school, in government, and in other settings. Computers and computer systems, including associated data storage, are increasingly being utilized to lower costs, increase productivity, provide security, and a host of other functions.

In the medical industry, the resources of medical professionals are increasingly spread in a variety of areas. In addition, demand for care has increased, while the supply, particularly of primary care physicians, has not. As a result, an alternative mechanism to meet medical need, such as providing remote contact with medical professionals for routine medical care, is needed. This alternative mechanism would help the medical professional better manage the increasing demand on their available resources, principally time, and allow for greater access to care for more patients. Currently, an effort is underway to facilitate medical consultations using computers and computing systems. This current effort, as of yet, has not fully addressed the need.

Providing health care in remote areas has been a challenge for decades. Traditionally, teams of healthcare professionals combine their talents and skills and engage in "missions" to areas where healthcare is required. These missions are limited in scope and duration, and generally rely on donations of time and equipment by the participants. Healthcare is only provided during the course of the missions, and follow-up care is rarely available for those in the area the mission visits. This has been the traditional method of first and second world nations providing healthcare to rural areas for many years, and there are few advances in this method.

SUMMARY OF THE INVENTION

In light of the foregoing, a need exists for tools allowing for the collection of medical data locally from a patient and supervision of a remote medical professional. In addition, a need exists for mechanisms whereby medical care may be provided to remote areas where accessibility to such care has been traditionally limited.

Accordingly, in one embodiment, by way of example only, a portable apparatus for orthopedic monitoring of a patient is provided. A housing is adapted for one of positioning adjacent to and positioning within an orthopedic cast. A diagnostic biomedical device integrated into the housing. The diagnostic biomedical device is adapted for obtaining an orthopedic image of a portion of the patient treated with the orthopedic cast. A wireless communications interface is coupled to the diagnostic biomedical device. The wireless communications interface is adapted to upload the orthopedic image to a remote server to be viewed by a medical professional.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict exemplary embodiments of the invention and are not therefore to be considered to be limiting of its scope, the invention will be described and explained with additional specificity and detail through the use of the accompanying drawings, in which.

DETAILED DESCRIPTION OF THE DRAWINGS

Figure 1:
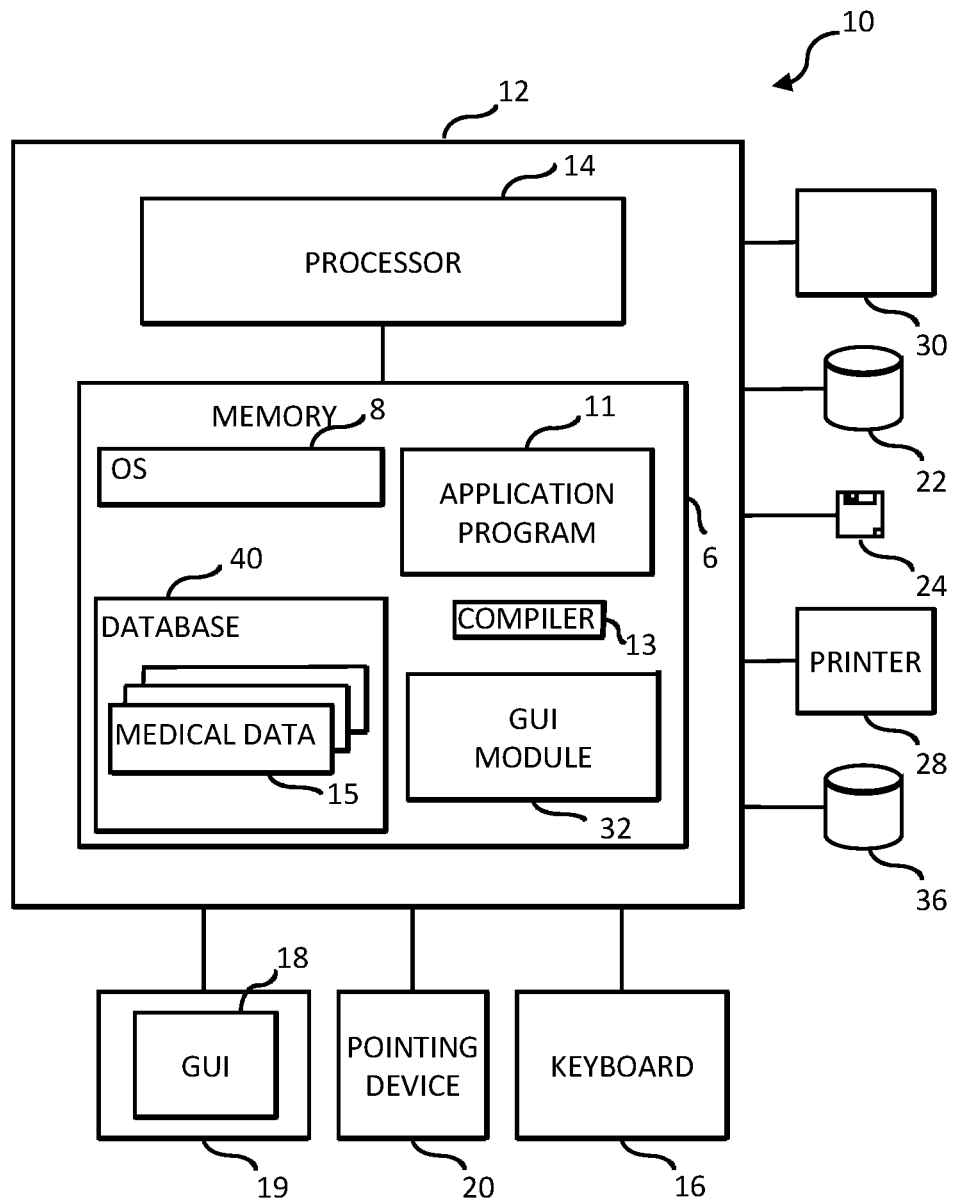
FIG. 1 illustrates an exemplary computing environment of which aspects thereof may be incorporated into embodiments of the present invention.

The illustrated embodiments below provide mechanisms for remote delivery and monitoring of healthcare to patients. For example, in one embodiment, health dermatological health information is obtained using a specialized device and conveyed to a medical professional for remote diagnosis and monitoring purposes. In an additional embodiment, orthopedic health information is obtained using an additional specialized device and conveyed to a medical professional for monitoring purposes. In still an additional embodiment, an apparatus is delivered to a rural or remote area. The apparatus includes tools for obtaining medical data and treatment under the supervision of a medical professional. In each of the illustrated embodiments, the medical information is obtained from the patient without the need for onsite medical attendance of the medical professional. This frees the medical professional's resources to be spread across a greater area, and allows the delivery of medical care to locations where access by a medical professional has typically been difficult or impossible.

Embodiments of the invention may be described herein in terms of functional and/or logical block components and various processing steps. It should be appreciated that such block components may be realized by any number of hardware, software, and/or firmware components configured to perform the specified functions. For example, an embodiment of the invention may employ various integrated circuit components, e.g., memory elements, digital signal processing elements, logic elements, look-up tables, or the like, that may carry out a variety of functions under the control of one or more microprocessors or other control devices. In addition, those skilled in the art will appreciate that embodiments of the present invention may be practiced in conjunction with any number of data transmission and data formatting protocols and that the system described herein is one example embodiment of the invention.

For the sake of brevity, conventional techniques related to signal processing, data transmission, signaling, network control, the 802.11 family of specifications, wireless networks, additional communications systems and specifications, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the invention.

The following description refers to elements or nodes or features being "connected" or "coupled" together. As used herein, unless expressly stated otherwise, "connected" means that one element/node/feature is directly joined to (or directly communicates with) another element/node/feature, and not necessarily mechanically. Likewise, unless expressly stated otherwise, "coupled" means that one element/node/feature is directly or indirectly joined to (or directly or indirectly communicates with) another element/node/feature, and not necessarily mechanically. The term "exemplary" is used in the sense of "example," rather than "model." Although the figures may depict example arrangements of elements, additional intervening elements, devices, features, or components may be present in an embodiment of the invention.

Turning to FIG. 1, an exemplary computer environment 10 in which aspects thereof may be incorporated into one or more embodiments of the present invention as will be further described is illustrated. Environment 10 includes a computer 12. The computer 12 comprises a processor 14 and a memory 6, such as random access memory (RAM). The computer 12 is operatively coupled to a display 19, which presents images such as windows to the user on a graphical user interface 18. The computer 12 may be coupled to other devices, such as a keyboard 16, a mouse device 20, a printer 28, etc. Of course, those skilled in the art will recognize that any combination of the above components, or any number of different components, peripherals, and other devices, may be used with the computer 12.

Generally, the computer 12 operates under control of an operating system (OS) 18 (e.g. z/OS, OS/2, LINUX, UNIX, WINDOWS, MAC OS) stored in the memory 6, and interfaces with the user to accept inputs and commands and to present results to the patient, for example through a graphical user interface (GUI) module 32. In one embodiment of the present invention, the OS 18 executes an application program 11 to gather medical information from a patient. Although the GUI module 32 is depicted as a separate module, the instructions performing the GUI functions can be resident or distributed in the operating system 18, the application program 11, or implemented with special purpose memory and processors.

Computer 12 includes a database 40. Database 40 may store a variety of relational information associated with patients, including vital information, medical histories, drug interactions, treatment instructions, and the like. Accordingly, database 40 is shown including a number of medical data files 15. Each of the medical data files 15 may be accessed by the database 40 using application program 11, for example. The skilled artisan will appreciate that application program 11, database 40 and medical data files 15 may vary in configuration and functionality according to a particular implementation.

The computer 12 also implements a compiler 13 that allows an application program 11 written in a programming language such as COBOL, PL/1, C, C++, JAVA, ADA, BASIC, VISUAL BASIC or any other programming language to be translated into code that is readable by the processor 14. After completion, the computer program 11 accesses and manipulates data stored in the memory 6 of the computer 12 using the relationships and logic that was generated using the compiler 13. The computer 12 also optionally comprises an external data communication device 30 such as a modem, satellite link, Ethernet card, wireless link or other device for communicating with other computers, e.g. via the Internet or other network.

Data storage device 22 is a direct access storage device (DASD) 22, including one or more primary volumes holding a number of datasets. DASD 22 may include a number of storage media, such as hard disk drives (HDDs), tapes, and the like. Data storage device 36 may also include a number of storage media in similar fashion to device 22. The device 36 may be designated as a backup device 36 for holding backup versions of the number of datasets primarily stored on the device 22. As the skilled artisan will appreciate, devices 22 and 36 need not be located on the same machine. Devices 22 may be located in geographically different regions, and connected by a network link such as Ethernet. Devices 22 and 36 may include one or more volumes, with a corresponding volume table of contents (VTOC) for each volume.

In one embodiment, instructions implementing the operating system 8, the computer program 11, and the compiler 13, as well as the database 40 and medical data fileset 14 are tangibly embodied in a computer-readable medium, which may include one or more fixed or removable data storage devices, such as a zip drive, disc 24, hard drive, DVD/CD-ROM, digital tape, etc., which are generically represented as the disc 24. Further, the operating system 8 and the computer program 11 comprise instructions which, when read and executed by the computer 12, cause the computer 12 to perform the steps necessary to implement and/or use the present invention. Computer program 11 and/or operating system 8 instructions may also be tangibly embodied in the memory 6 and/or transmitted through or accessed by the data communication device 30. As such, the terms "article of manufacture," "program storage device" and "computer program product" as may be used herein are intended to encompass a computer program accessible and/or operable from any computer readable device or media.

Embodiments of the present invention may include one or more associated software application programs 11 that include, for example, functions for managing a distributed computer system comprising a network of computing devices, such as a storage area network (SAN). Accordingly, processor 14 may comprise a storage management processor (SMP). The program 11 may operate within a single computer 12 or as part of a distributed computer system comprising a network of computing devices. The network may encompass one or more computers connected via a local area network and/or Internet connection (which may be public or secure, e.g. through a virtual private network (VPN) connection), or via a fibre channel SAN or other known network types as will be understood by those skilled in the art. (Note that a fibre channel SAN is typically used only for computers to communicate with storage systems, and not with each other.) As one skilled in the art will appreciate, however, various additional components of the environment 10 may work individually or in concert to define, initialize, and perform the functionality for facilitating deduplication product testing as will be further described.

In one of the illustrated embodiments, an on-demand, self-sustaining and self-sufficient advanced medical unit is provided for implementation in emerging/developing markets. An exemplary unit may include an unmanned structure, such as a shipping container, which contains all the instrumentation required to conduct a particular set of medical tests. Users of the apparatus enter the structure, provide personal credentials, and then have certain tests or medical procedures executed depending on need. Data would be collected by the apparatus and transmitted electronically in a secured manner to medical professionals, such as doctors, for analysis.

Diagnoses by the medical professional may be transmitted back to the apparatus for retrieval by the user at a later date. All patient data is secure, encrypted, and private. Medical equipment in the structure is secured in such a way as to prevent vandalism. Sterilization of the medical equipment would be automatic. The structure could easily be moved from one area to another via methods such as truck transport or helicopter transport. Power to the structure is provided by a sustainable, stand-alone method such as solar cells, yet also allows for local power connections.

The standalone apparatus described above advances providing medical care to areas where access to traditional medicine has been limited or nonexistent. First, the apparatus is unmanned, which reduces costs necessary to support onsite personnel. Second, the apparatus is automated, which reduces the chances for human error and contamination in the collection of medical samples. Third, the apparatus is sustainable through the use of self-contained, onboard power. Fourth, the apparatus is expeditious, as information is transmitted on a frequent basis for review by offsite medical staff. Finally, the apparatus is mobile, and can be moved to many areas over time, providing a broader reach of medical care than currently possible.

In one exemplary embodiment, the standalone apparatus described above is capable of being transported to various locations, using means such as truck, train, helicopter, or ship. The apparatus is housed in a shelter similar in size to a shipping container of the sort that are routinely used for exporting goods from various countries, and which can be seen stacked on trains and ships throughout the world. Equipment necessary to provide unmanned healthcare is installed within the container.

To assist the apparatus described above in providing unassisted, stand-alone healthcare, a renewable, self-contained power source for powering the apparatus may be integrated. Such a power system may include solar energy panels, an internal generator, or battery. A power connection for external attachment, in the event that external power is available, may also be included. Finally, a communication center for collecting and transmitting information to reviewing medical professionals may implement several communications mechanisms such as WiFi, Internet, Satellite, and cellular communications protocols. As will be further described, the patient area portion of the apparatus may be adapted for collection of patient data (such as vital statistics and the like), as well as for administration of healthcare related items (such as vaccines, medications, etc.).

Figure 2:
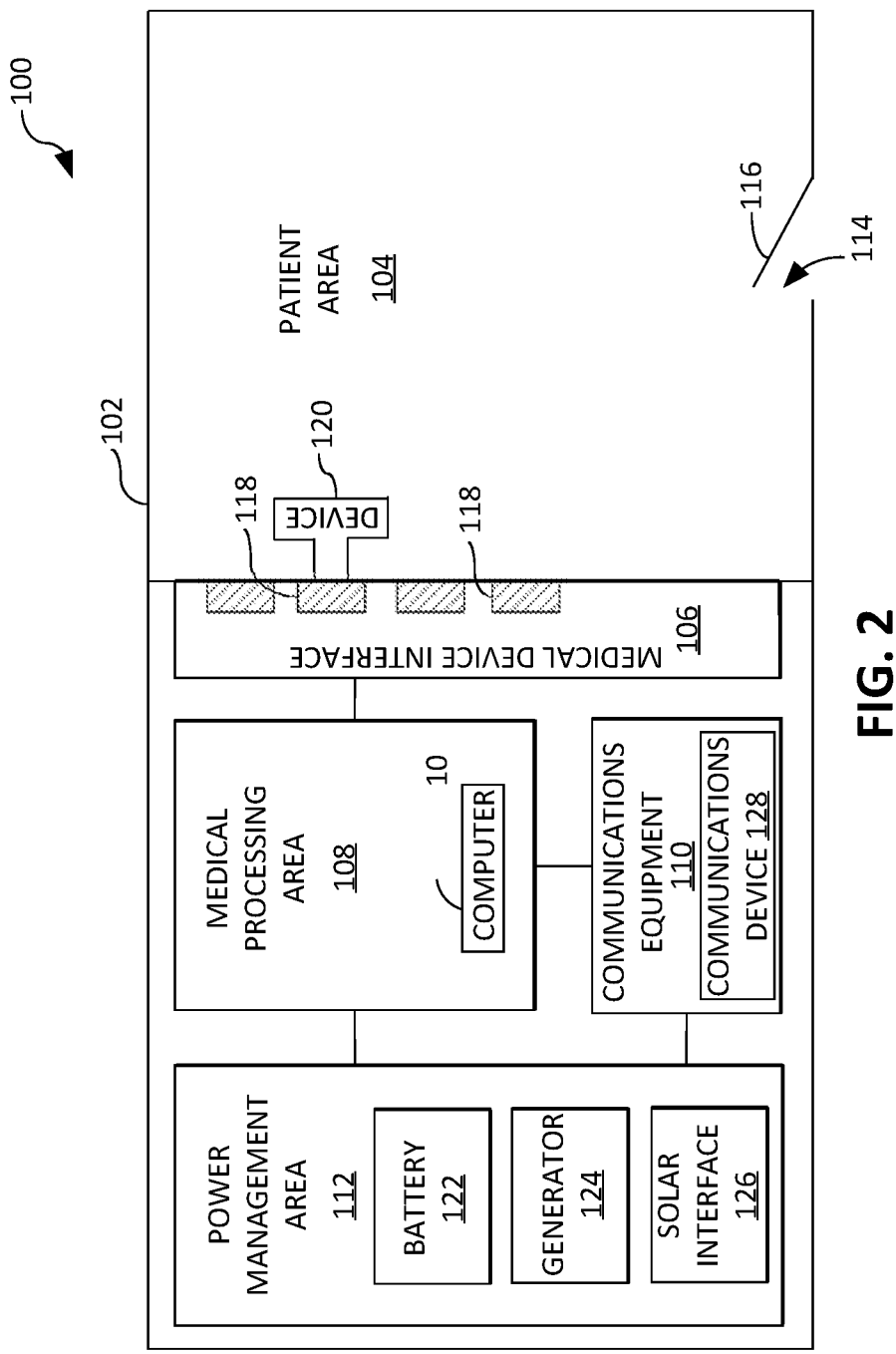
FIG. 2 illustrates an exemplary apparatus for providing medical care to rural and remote areas.

Turning to FIG. 2, an exemplary apparatus 100 for providing medical care in remote and rural areas as described previously is illustrated in block diagram format. Apparatus 100 includes a container 102 or similar housing. Container 102 may be comprised of a corrugated steel material typically used in shipping containers to provide strength. As the skilled artisan will appreciate, a variety of additional materials may be implemented. Container 102 houses a patient area 104. A patient accesses the patient area through a door 116 (illustrated through arrow 114). The patient may interact with the apparatus to provide or collect medical information, and receive treatment inside patient area 104. Embodiments may include places for the patient to sit (not shown), provide samples, and otherwise interact with the apparatus 100.

A medical device interface 106 portion provides an interface between the medical processing area 108 and the patient area 104. Interface 106 includes several communications ports 118 in which one or more input devices 120 tailored to the region of deployment are modularly connected. Examples of such input devices 120 will be described further, following. Medical processing area includes a computer environment 10 such as the environment 10 depicted in FIG. 1 with specialized application to gathering, processing, and dispensing medical information and treatment. Again, as the skilled artisan will appreciate, the particular components of environment 10 will vary according to a particular implementation. For example, the computer environment 10 may include necessary electronics equipment for processing samples collected in the patient area 104.

Medical processing area 108 is also connected to communications equipment 110 and power management area 112. Power management area 112 performs power functions for the apparatus 100. Power management area may include a variety of power sources, such as one or more onboard batteries 122, a generator 124, and/or a solar interface 126. Power management area may be adapted to supply all of the power needs for the apparatus 100, including the components in computer environment 10 and devices 120 connected to the medical device interface 106. Alternatively, power management area 10 may include equipment allowing the connection of the apparatus 100 to the local power grid.

Communications equipment 110 includes one or more communications devices 128 providing the functionality necessary to send/receive communications to/from offsite medical personnel. Portions of the computer environment 10 may be used as or in conjunction with communications equipment 110. Communications equipment may include devices such as cellular devices, WiFi, Internet, Voice Over Internet Protocol (VOIP), and similar devices to allow for the exchange of information between apparatus 100 and the medical professional.

Figure 3:
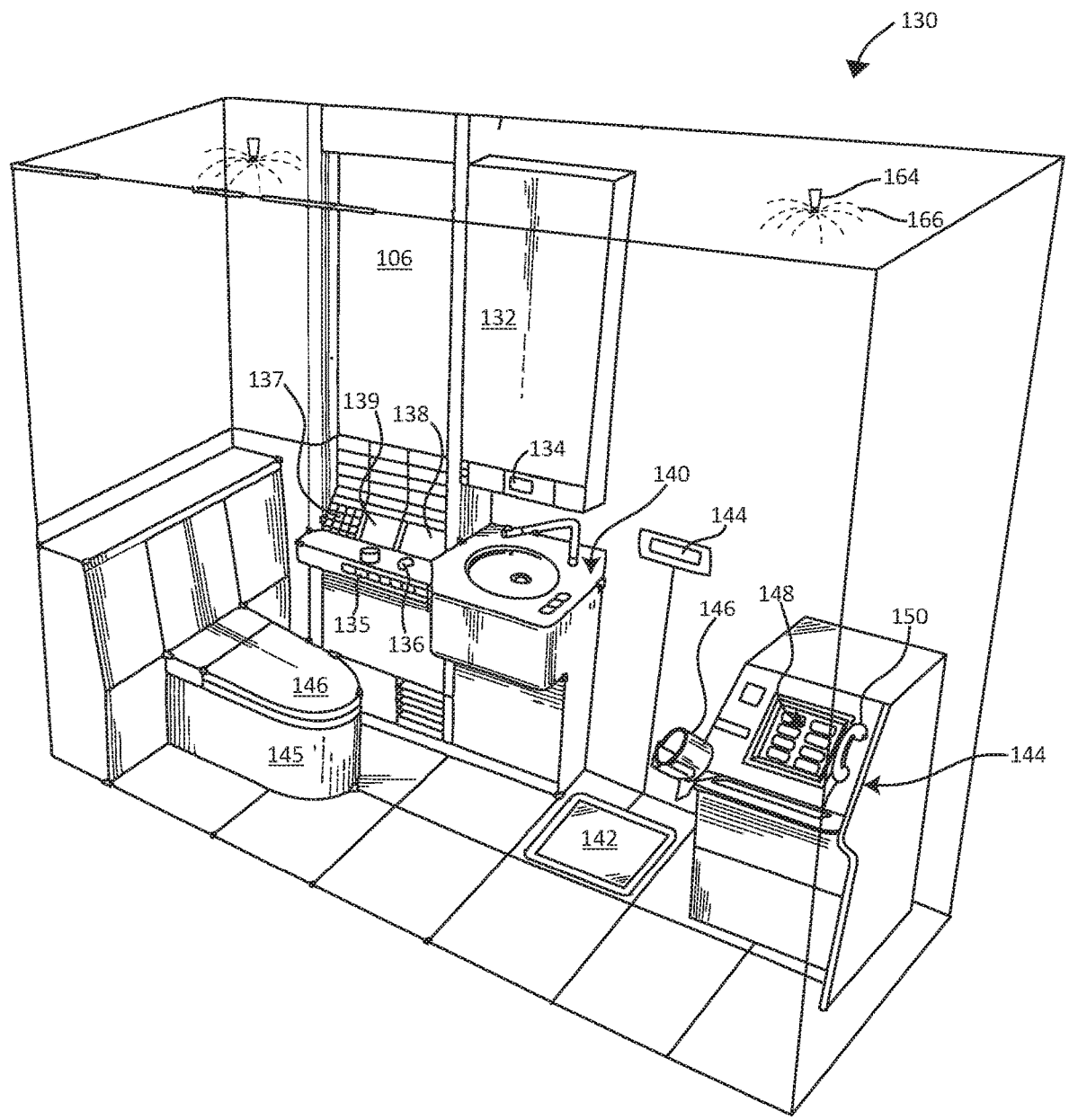
FIG. 3 illustrates an exemplary patient area of the apparatus depicted in FIG. 2.

Turning to FIG. 3, an exemplary interior 130 of a patient area is illustrated. Interior 130 includes a variety of equipment necessary to collect and analyze information, and dispense treatment to a patient. Interior 130 as illustrated includes several exemplary medical sampling and treatment devices that are operable by the patient and observable remotely under the supervision of the medical professional. GUI interface 144 includes a platform for the collection of medical information with an integrated GUI display 148 and communications device 150, in this case, a telephone device. In other exemplary embodiments, communications device 150 may include such devices as cameras and imaging devices, microphones, keyboards, and other input devices (not shown). Further, GUI display 148 may be adapted to be touch sensitive for collection of patient input. A cuff device 146 is provided for obtaining medical data such as a patient's blood pressure. For the sake of convenience, a chair or other seating device in which the patient is seated is not shown.

GUI interface 144 is an example of one or more modular devices that are connectable into the medical device interface. Other exemplary devices are additionally shown, including a scale 142 and interconnected display 144 for obtaining weight information, and a dispensary 132. Dispensary 132 is adapted for dispensing treatment related items, such as first-aid materials 134 which may be obtained by the patient. Dispensary 132 may be adapted for providing a variety of health care related items, as the skilled artisan will appreciate. Below dispensary 132 is a lavatory 140 for use by a patient.

A commode 146 is provided. Commode 146 may be adapted to obtain samples of medical data, such as a urine sample, internally (shown by reference number 145). An additional interface device 106 is located between the commode 146 and the lavatory 140 for patient interaction. Interface device 106 may include an additional GUI 139 for providing visual cues to the patient, as well as input buttons 135 and 137. Interface 106 may also include a collection window 138 for obtaining samples from the patient and/or dispensing functionality. For example, window 138 may dispense certain drugs 136, vaccines, and the like depending upon a particular patient input, sample analysis, interaction with the medical professional, etc.

Two dispensers 164 of sterilization material 166 are incorporated into the ceiling of the interior 130 to provide for automated sterilization functionality of the interior 130 once the patient concludes treatment. Such automated sterilization functionality may be enabled once the patient opens and closes the door, and the apparatus has determined that the patient has exited the patient area.

Figure 4:
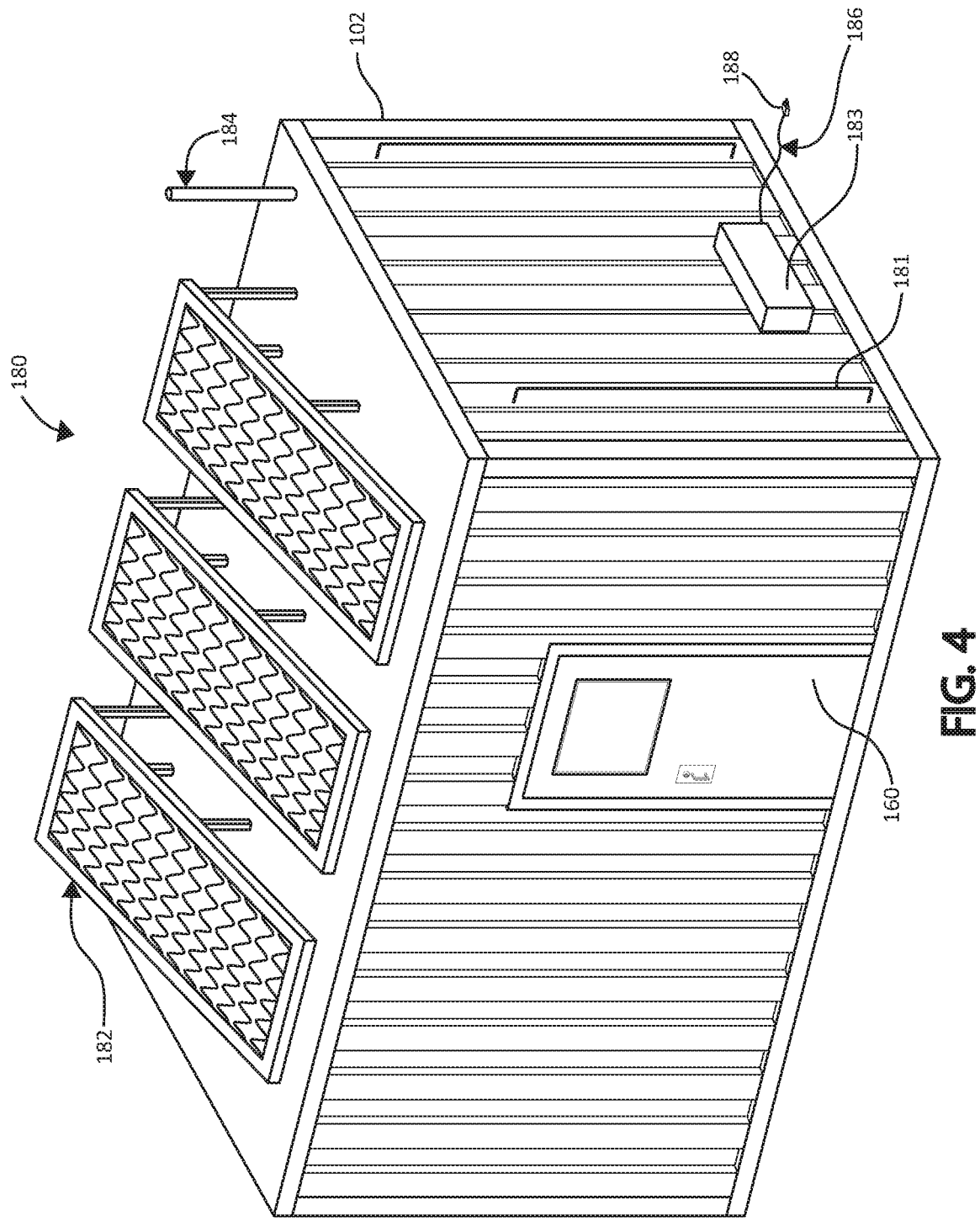
FIG. 4 illustrates an exterior view of the exemplary apparatus depicted in FIG. 2.

Turning to FIG. 4, an external view 180 of the apparatus 100 (FIG. 2) is depicted. Container 102 is comprised of corrugated steel, with handles 181 provided for ease of commercial shipment. Power supply 183 is connected internally to power management area 112 (FIG. 2) for external connection 186 of electrical power via plug 188. A door 160 includes a handle and lock mechanism to allow for secure entry and treatment of the patient inside. Several solar panels 182 are arranged along the top portion of the apparatus for collection of solar rays. The solar panels 182 are also connected internally to the power management area. Finally, an antenna 184 is connected internally to the communications equipment 110 (FIG. 2) for sending and receiving information as the skilled artisan will appreciate.

Figure 5:
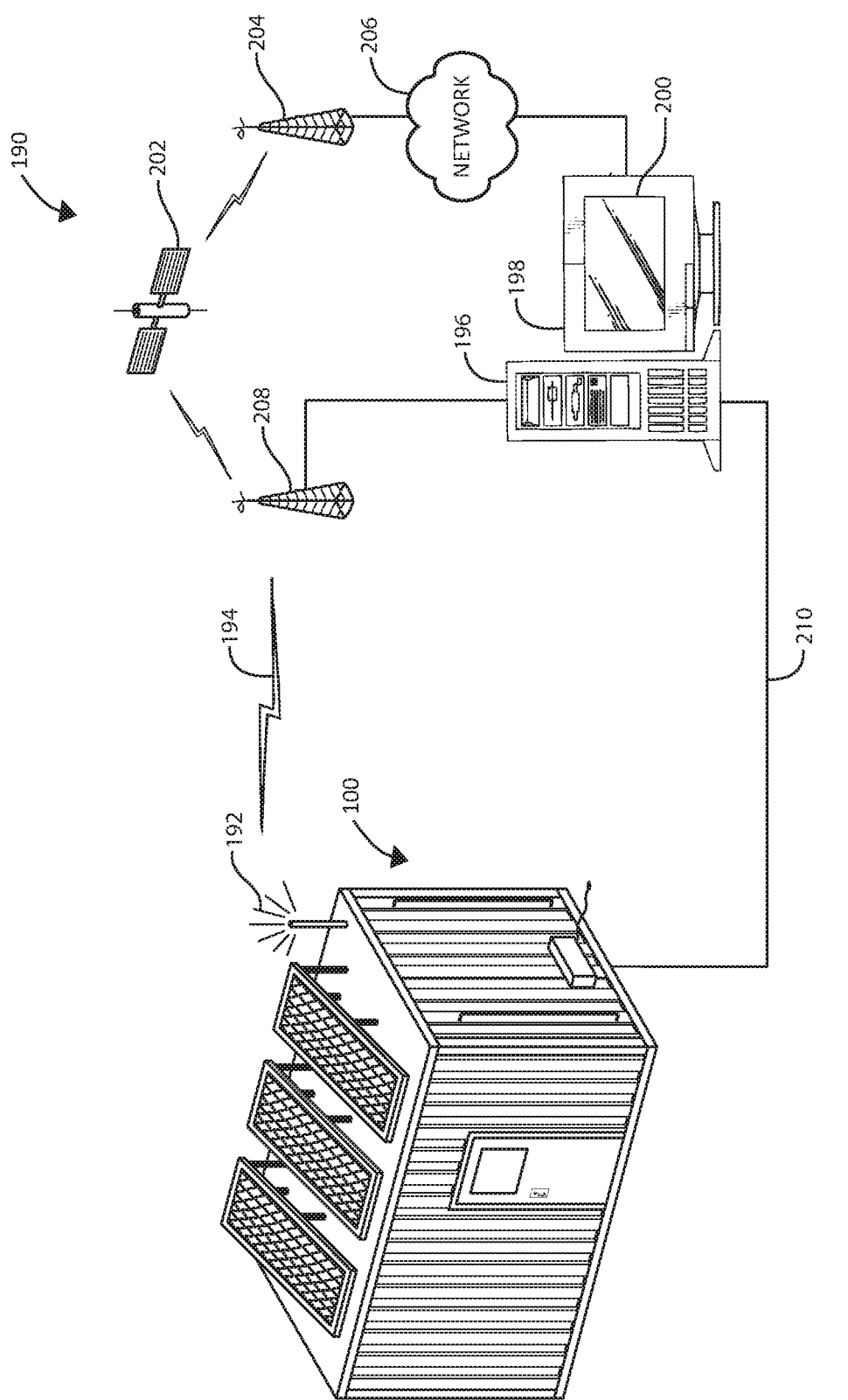
FIG. 5 illustrates a system of communication between the apparatus depicted in FIG. 2 and a remote server accessible by a medical professional.

FIG. 5 illustrates an exemplary system 190 of communication between the apparatus 100 and a remote server accessible by the medical professional. The apparatus 100 may implement wireless signals 192, 194 which are collected and transmitted by transceiver 208 as illustrated via the depicted communications paths. Satellite communication may relay the wireless signals 192, 194 to an additional transceiver 204, where it is transmitted over network 206 (such as the World Wide Web or a local Intranet or Extranet) to the remote server 196. The transceiver 208 may also send the communication directly to the remote server 196. Alternatively still, the apparatus 100 may be hard-wired to the remote server 196. In each case, data, images, information, voice and/or auditory communication, etc. may be relayed to/from the apparatus to/from the remote server 196 where it may be viewed on display 198 and shown on display 200.

As the skilled artisan will appreciate, the illustrated communications paths may include a variety of communications mechanisms. For example, the paths may be compliant with a universal serial bus (USB) communications protocol, an internet protocol (IP), an Institute for Electrical and Electronics Engineers (IEEE) wired or wireless communications protocol, a wireless application protocol (WAP), a local area network (LAN) protocol, a wide area network (WAN) protocol, a global system for mobile communication (GSM) protocol, and an AppleTalk® protocol.

An exemplary method of operation of the apparatus 100 may proceed as follows. As a first step, the apparatus is placed (such as commercially shipped or dropped) in a rural or remote area, or in emerging/developing markets for health care. Depending on the particular region, the container may be updated with all necessary interfaces, including software, power, and medical necessities required to accommodate particular health needs. The patient then makes a trip to the apparatus for personal healthcare management. The patient enters the apparatus, and door is locked for personal security. The patient seats himself or herself in the patient area, where he or she interacts with the apparatus. The following may occur: (1) input of patient data such as name, age, address, etc., (2) input of patient symptoms or concerns (this could be via pictograms, for more common ailments, through the use of a keyboard, for more detailed descriptions, or perhaps through a video recording of a patient narrative), (3) automated, unmanned collection of vital data such as temperature, weight, blood pressure, (4) automated, unmanned collection of blood, saliva, urine, stool samples or other bodily fluids, and (5) automated, unmanned dispensing of drugs, vaccines, and other treatments appropriate to the device. The apparatus may analyze, and later destroy, collected samples. Information representative of the samples may then be transmitted via the communications equipment. After patient has completed their visit, the door is unlocked, and the next patient is free to enter.

Additional embodiments may make possible the use of remotely administered healthcare. Such an additional embodiment may assist in the monitoring and treatment of dermatological issues. Currently, most dermatological care is provided through in-office doctor visits. Of these visits most consist of routine check-ups, which are administered by a dermatologist. For many people dermatological care is seldom, if ever sought out. But for patients that have higher risks for skin diseases, based on personal and/or family histories, these visits can come once every six months, or even more frequently, especially for those that have many non-routine/unscheduled visits.

To help reduce cost and improve healthcare resource allocation associated with dermatological issues, a mechanism may be implemented whereby a patient may convey dermatological information, particularly routinely collected information, to the medical professional at a remote location for analysis. In one embodiment, this mechanism allows patients to perform in-home dermatological examinations using a portable device, which uploads high resolution pictures to electronic data repositories owned and operated by their dermatologists' offices.

In one embodiment, an apparatus is provided allowing for in-home dermatological monitoring through a portable, wireless, and reusable device. The patient obtains the device from their dermatologist's office, preprogrammed to connect wirelessly to a specific upload location. Alternatively, the device can be bought from a retail outlet, and easily programmed by the user to connect to a particular image upload location. In the privacy of their own home, the patient uses the device to take pictures of the area(s) of skin where there is/are concerns. The device may photograph as large an area of the body as needed by taking multiple images. Once the images are captured, the patient initiates an upload, and will be alerted when the upload is complete. The patient's dermatologist can then view and assess the images from their local machine, or through remote access. Such a device helps to make dermatological care more efficient, while being extremely easy to use for patients and doctors. Anyone with or without technical knowledge should be able to use the device without difficulty.

The device may feature a portable, rechargeable, and small footprint. Only a few large buttons may be located on the device to improve ease of use. The device may include a built-in flash memory for temporarily storing images. For security purposes, all images may be deleted upon successful upload. An indicator light (such as a blue light) may illuminate when at least one image is stored on local memory. An additional indicator light (such as a green light) may illuminate when the image(s) are successfully uploaded and deleted locally.

A high-resolution imaging device, such as but not necessarily limited to, a camera, is integrated into the device and specially adapted for capturing macro images. Additionally, software installed on the device, such as an anti-motion algorithm, may be applied to the images to improve quality. A lighting mechanism may also be incorporated for improving quality and capturing high-resolution dermatological images. Finally, the device may use a number of wireless mechanisms to communicate the image data to the medical professional.

Figure 6:
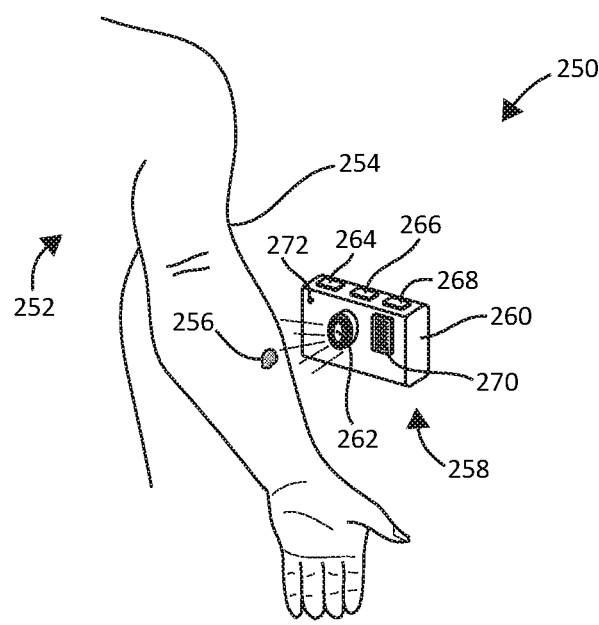
FIG. 6 illustrates a device for obtaining dermatological images for remote view by a medical professional.

Turning now to FIG. 6, a system 250 for capturing dermatological images of a patient using an exemplary device 258 is shown in view of the foregoing discussion. Device 258 includes a housing 260, a high-resolution imaging device and lens 262, a power button 264, a photo button 266, and an upload button 268. A specialized lighting device 270 is adapted for capturing macro dermatological images. One or more indicator lights provides status information to the patient 252.

As is shown, the device 258 is aimed at a dermatological issue 256 in question on the patient's arm 254, such as a skin lesion that is in the process of healing. The patient powers on the device by pressing the power button 264, and captures one or more dermatological images by pressing the photo button 266.

Figure 7:
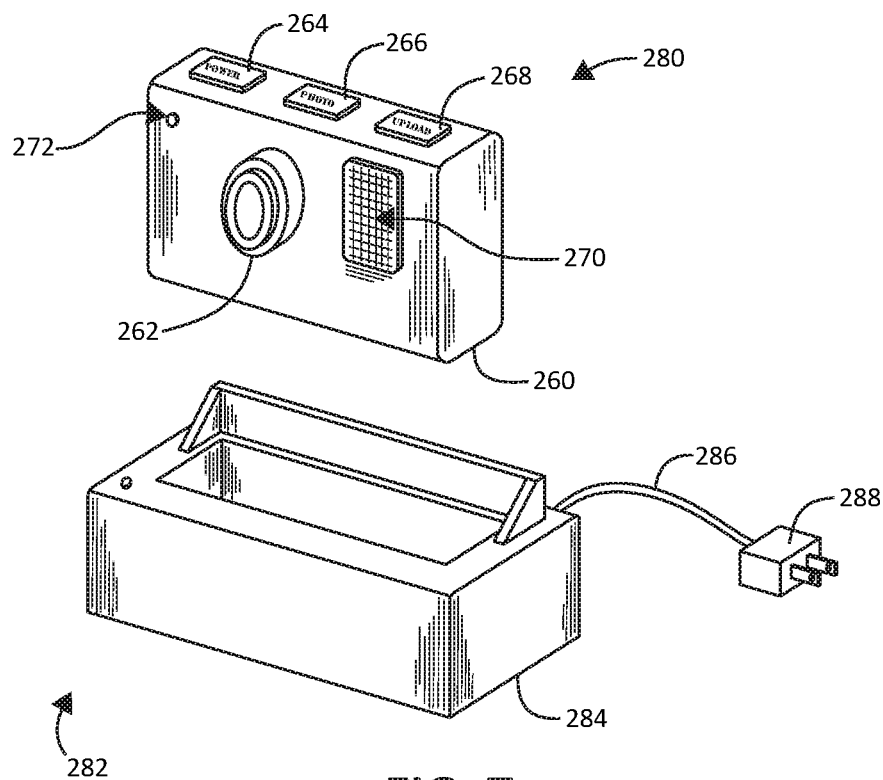
FIG. 7 illustrates charging functionality of the device illustrated in FIG. 6.

FIG. 7 illustrates a more detailed view of the device, illustrating a charging system 280. The exemplary device shown in FIG. 6 is again illustrated, including buttons 264, 266, and 268, imaging device 262, indicator light(s) 272, and specialized lighting device 270. A charging device 282 includes a housing 284 adapted for receiving the housing 260 of the device. A power cord 286 and plug 288 supplies power to the charging system.

Figure 8:
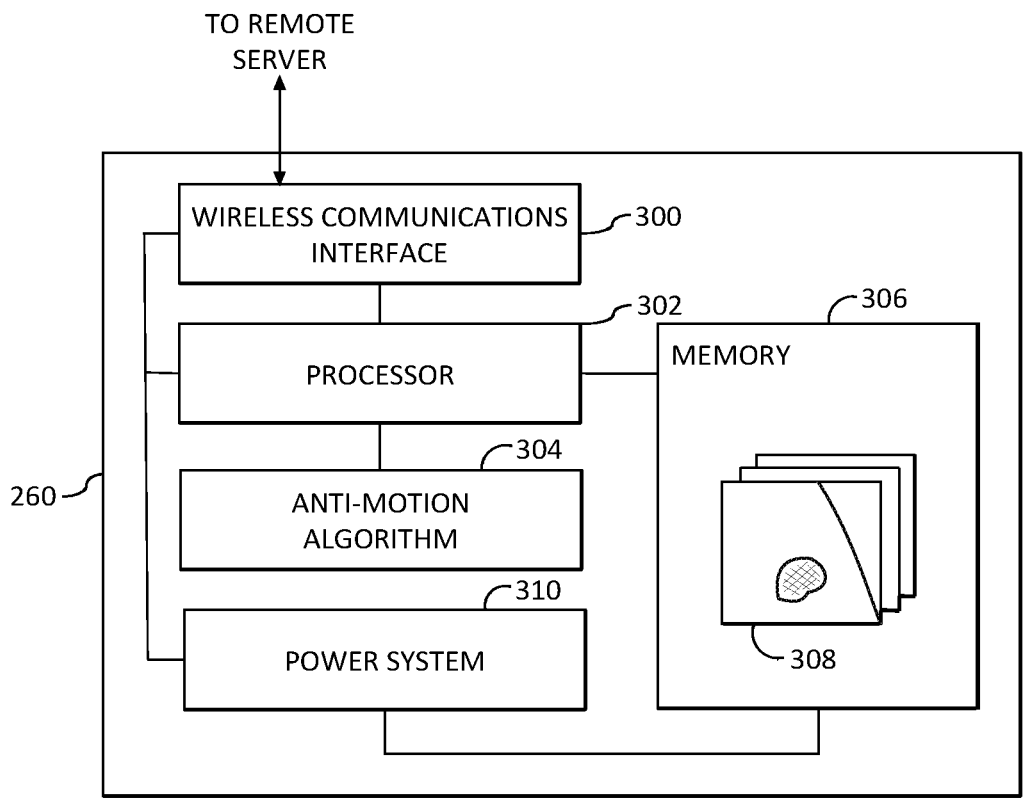
FIG. 8 illustrates exemplary internal electronic components of the device illustrated in FIG. 6.

Exemplary electronic components of the device are illustrated in FIG. 8 in block diagram form. As was previously mentioned, some of the components in computing environment 10 (FIG. 1), such as memory, processing, operating systems, and the like may be adapted and incorporated for the specialized purpose of obtaining dermatological images. The device 258 includes a wireless communications interface 300 for communication to/from a remote server. Wireless communications interface 300 may be adapted for use and compatibility with the variety of previously mentioned communications mechanisms. A processor 302 is adapted for processing images captured by the imaging device 312. An anti-motion algorithm 304 may be applied to the processing of the images (whether during the capturing phase or post capture) to enhance image quality. The images 308 are stored in a memory location 306.

Figure 9:
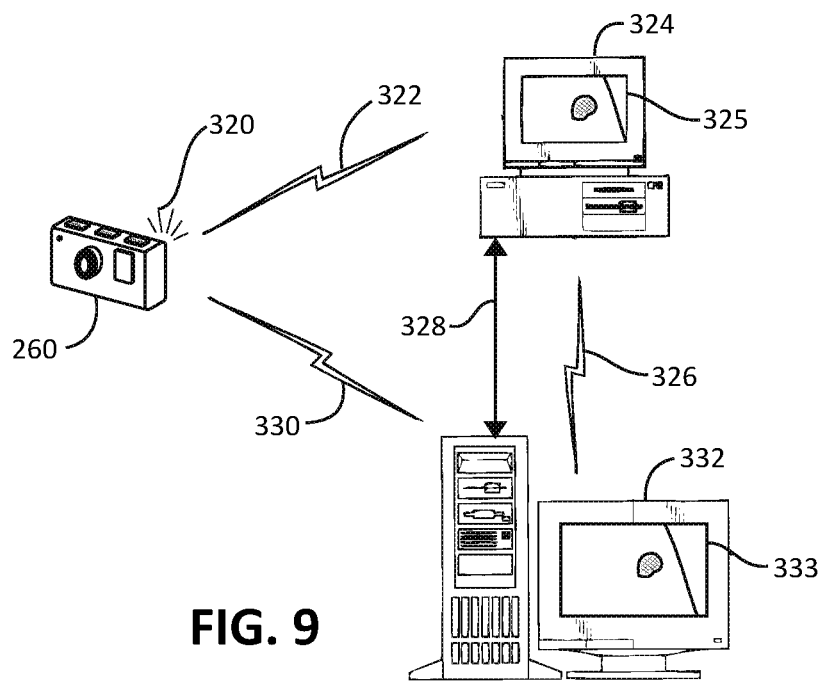
FIG. 9 illustrates an additional system of communication between the device illustrated in FIG. 6 and remote servers accessible by a medical professional.

FIG. 9 illustrates an additional exemplary system of communication between the device 258 and remote servers accessible by a medical professional, such as a dermatologist. The wireless communications interface, upon a depression of the upload button, uses wireless signals 320, 322, and 330, which are transmitted to one or more remote servers 340 and 342. In one embodiment, the remote server 340 is located proximately to the patient, such as the patient's home computer. The server 340 then transmits the image data across communications path 328 to the server 342 in the medical professional's office. In both or either case, the patient and/or the medical professional may view the images on GUI screens 325 and 333 as shown on displays 324 and 332.

Still additional embodiments may make possible the use of remotely administered healthcare. These additional embodiments may assist in the monitoring and treatment of orthopedic injuries. Currently when someone has a broken bone, many times healing of the bone requires cast setting. Normally, the medical professional is familiar with the bone being set and estimating a healing time. After the specified time the patient returns to the medical professional, the cast is removed and an X-ray has to be taken again to determine the state of the healing process. If the bone is not completely healed then a recast will be performed and the medical professional will again estimate the healing time. This process to evaluate the broken bone can take several attempts, incurring additional time and expense to the patient, the medical professional and insurance company. In addition, a certain amount of risk is involved with the unknowns of removing and resetting casts.

To reduce cost and resource use associated with routine visits to monitor orthopedic healing, exemplary embodiments as will be described may be implemented to assist in such tasks. One embodiment utilizes a reusable, portable, wireless orthopedic monitoring device. There are numerous possible advantages of such a device. Unnecessary visits to the medical professional are reduced or eliminated. The medical professional is able to monitor the healing process remotely. If a patient heals faster than expected, an office visit can be scheduled to remove the cast and begin any physical therapy. If the healing process is taking longer than expected, the device can remain on the patient until the doctor is ready to remove it. This not only saves money and materials associated with recasting, but also reduces some of the trauma associated with these types of office visits (particularly for children and elderly persons).

The embodiment uses a portable device that is strategically embedded into a reusable, portable, wireless orthopedic monitoring device. This device is positioned above the original fracture and obtains X-ray or ultrasound pictures/images of the healing bone. The device can be configured/programmed by the physician to take a predetermined number of images per day or per week. These images are then wirelessly uploaded using a wireless component embedded into the portable device to an Internet connected device in the patient's home, office or any other remote site. The internet connected device will then upload the same images to a remote data repository, owned and controlled by an orthopedic office. The images can be viewed remotely by the medical professional to monitor the healing process, who will be alerted quickly to problems. In addition, if the fracture being monitored has healed faster than expected, the patient can be relieved of this orthopedic monitoring device and rehabilitation can begin sooner.

Figure 10:
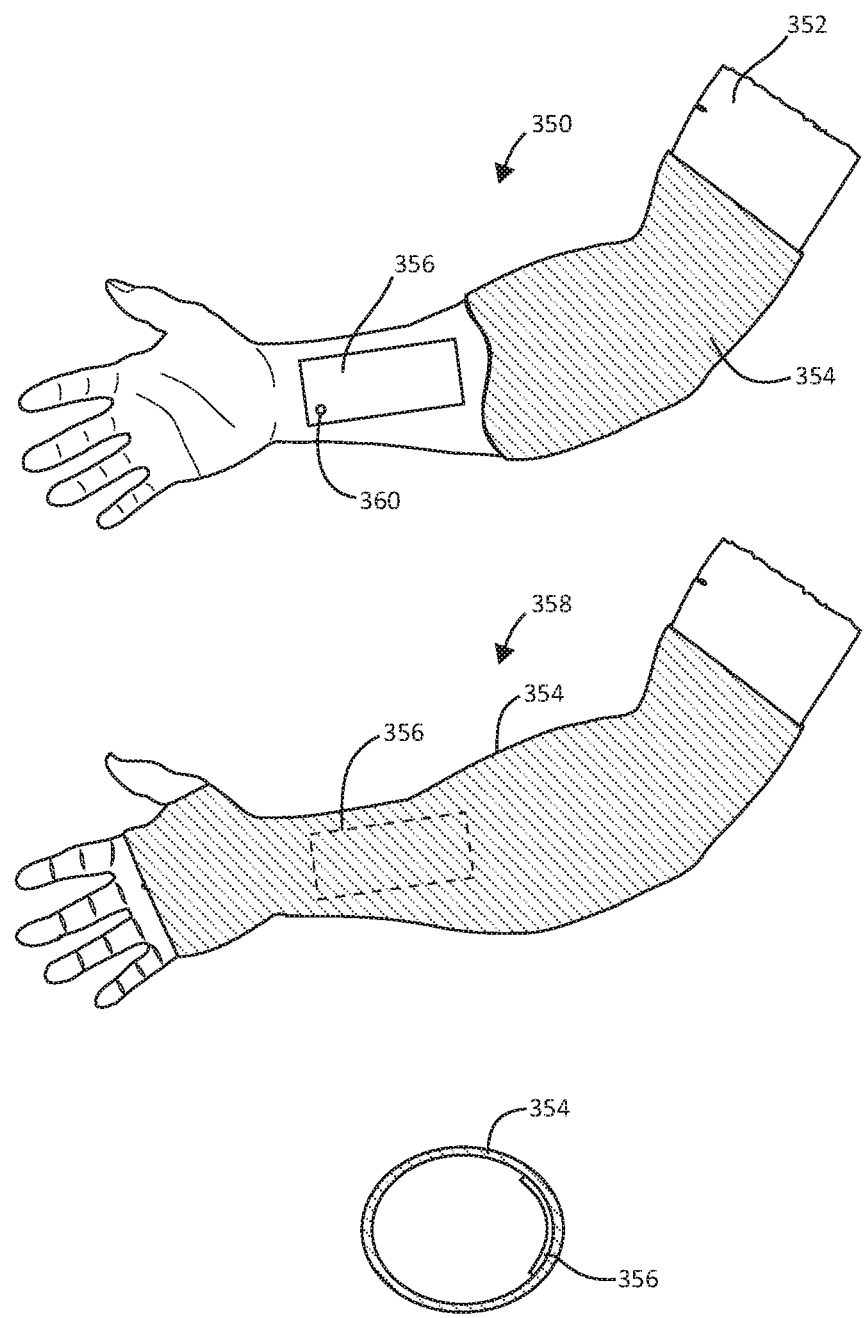
FIG. 10 illustrates various views of a device for obtaining orthopedic images of a patient.

The device described above may include such functionality as network connectivity, built-in wireless and/or cellular capability, a standby power component (where power to the device is regulated in a standby mode until images are obtained), and an accessible battery compartment for replacement of batteries. FIG. 10 illustrates several views 350, 358 of an exemplary such device 356. Device 356 is positioned adjacent to, or within the orthopedic cast 354 of a patient's arm 352. Device 356 includes one or more indicator lights 360 to indicate low battery power. In view 358, the device is positioned between the cast and the patient's skin. This is more clearly shown in the bottom, cross-sectional view, where device 356 is positioned interiorly to the cast 354.

Figure 11:
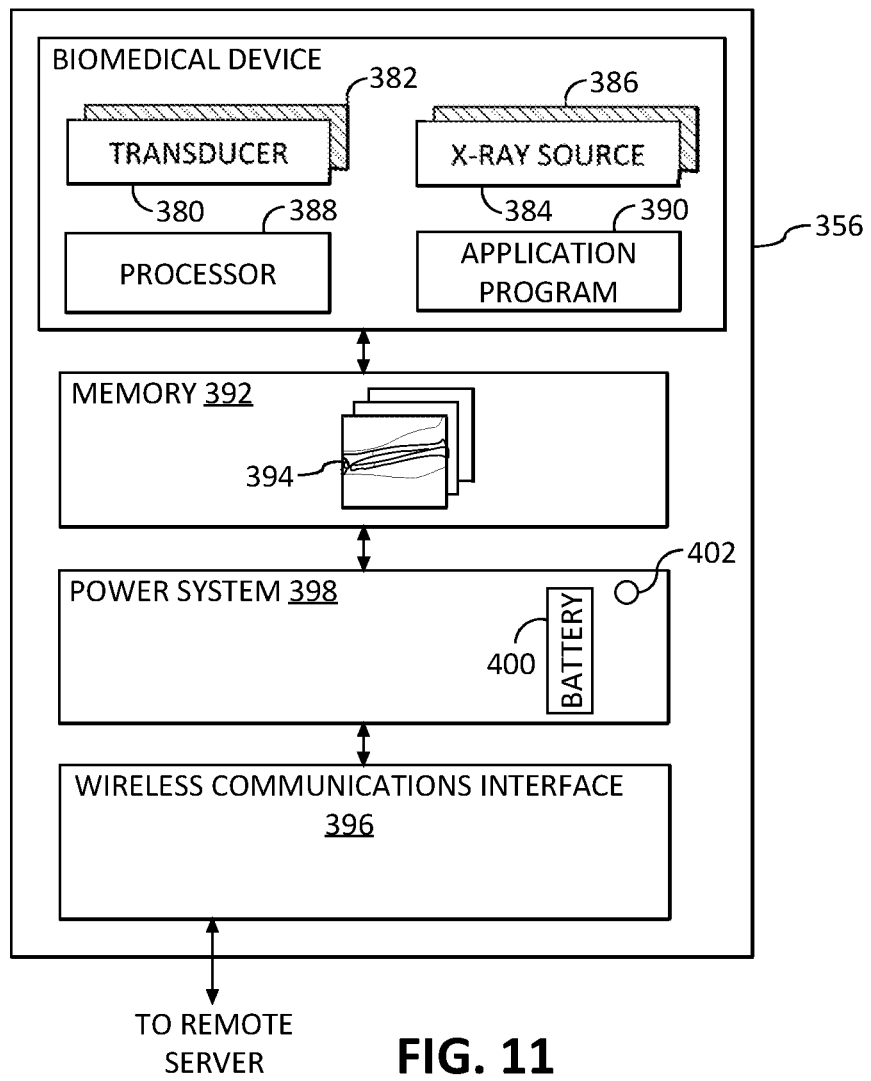
FIG. 11 illustrates exemplary internal components of the device illustrated in FIG. 10.

FIG. 11 illustrates exemplary electronic components of the device in block diagram form. As was previously mentioned, some of the components in computing environment 10 (FIG. 1), such as memory, processing, operating systems, and the like may be adapted and incorporated for the specialized purpose of obtaining orthopedic images. The device 356 includes a wireless communications interface 396 for communication to/from a remote server. Wireless communications interface 396 may be adapted for use and compatibility with the variety of previously mentioned communications mechanisms.

A power system 398 including a battery 400 and one or more indicator lights 402 is connected to the wireless communications interface 396. A memory 392 for storing orthopedic images 394 is connected to the power system 398 and a biomedical device 370. Biomedical device 370 is adapted for obtaining orthopedic images from the patient. Device 370 may include components for obtaining x-ray images and/or components for obtaining sonogram images of the patient. Accordingly, device 370 includes an acoustic transducer 380 for sending and receiving pulses of sound. An impedance-matching material 382 is positioned between the acoustic transducer and the housing of the device 356 to increase sound transfer efficiency. A processor 388 processes the received sound to generate sonogram images 394.

In similar fashion, an x-ray source and detector device 384 may also be incorporated. The x-ray source portion of source/detector 384 is shielded with a low-density insulating material 386 containing a high-Z substance. In either case of the x-ray source/detector 384 and transducer 380 devices, an application program 390 may be used with the assistance of processor 388 to generate the sonograms and/or x-ray images as the skilled artisan will appreciate. In one embodiment, the application program calendars a set schedule of days/times in which images of the patient will be obtained. The power system sets the biomedical device in a lower power/sleep mode of operation when the device is not active. Accordingly, the biomedical device may obtain a predetermined number of images according to a schedule set by the medical professional.

Figure 12:
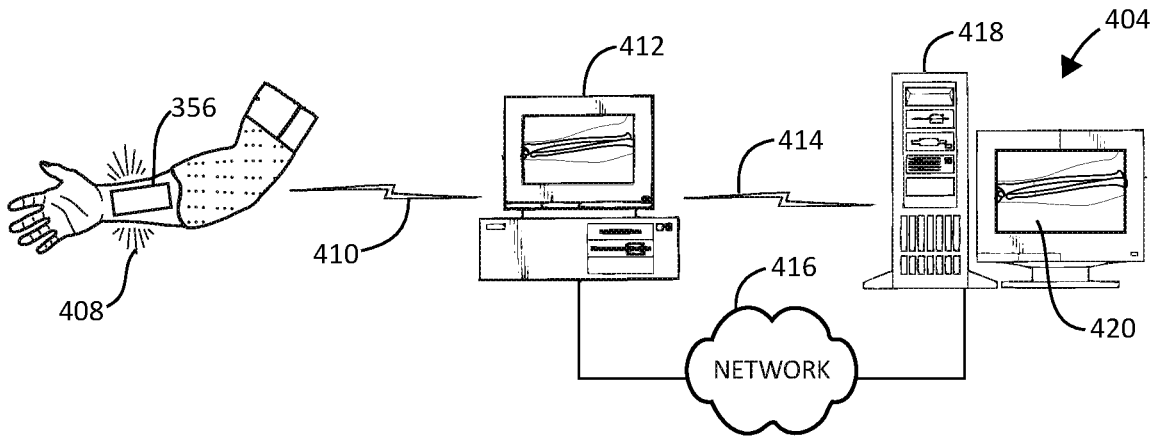
FIG. 12 illustrates an additional system of communication between the device illustrated in FIG. 10 and a remote server accessible by a medical professional.

FIG. 12 illustrates an additional exemplary system 404 of communication between the device 356 and a remote server accessible by a medical professional, such as a physician. The wireless communications interface, upon activation (such as directed by the application program, a wake up signal from computer 412, or another mechanism as the skilled artisan will appreciate), uses wireless signal 410 to convey orthopedic image data to computer 412. In one embodiment, the computer 412 is located proximately to the patient, such as the patient's home computer. The computer 412 then transmits the image data across network 416, or alternatively wirelessly using signal 414 to the server 418 in the medical professional's office. The medical professional may then view and analyze the orthopedic image shown on display 420.

Figure 13:
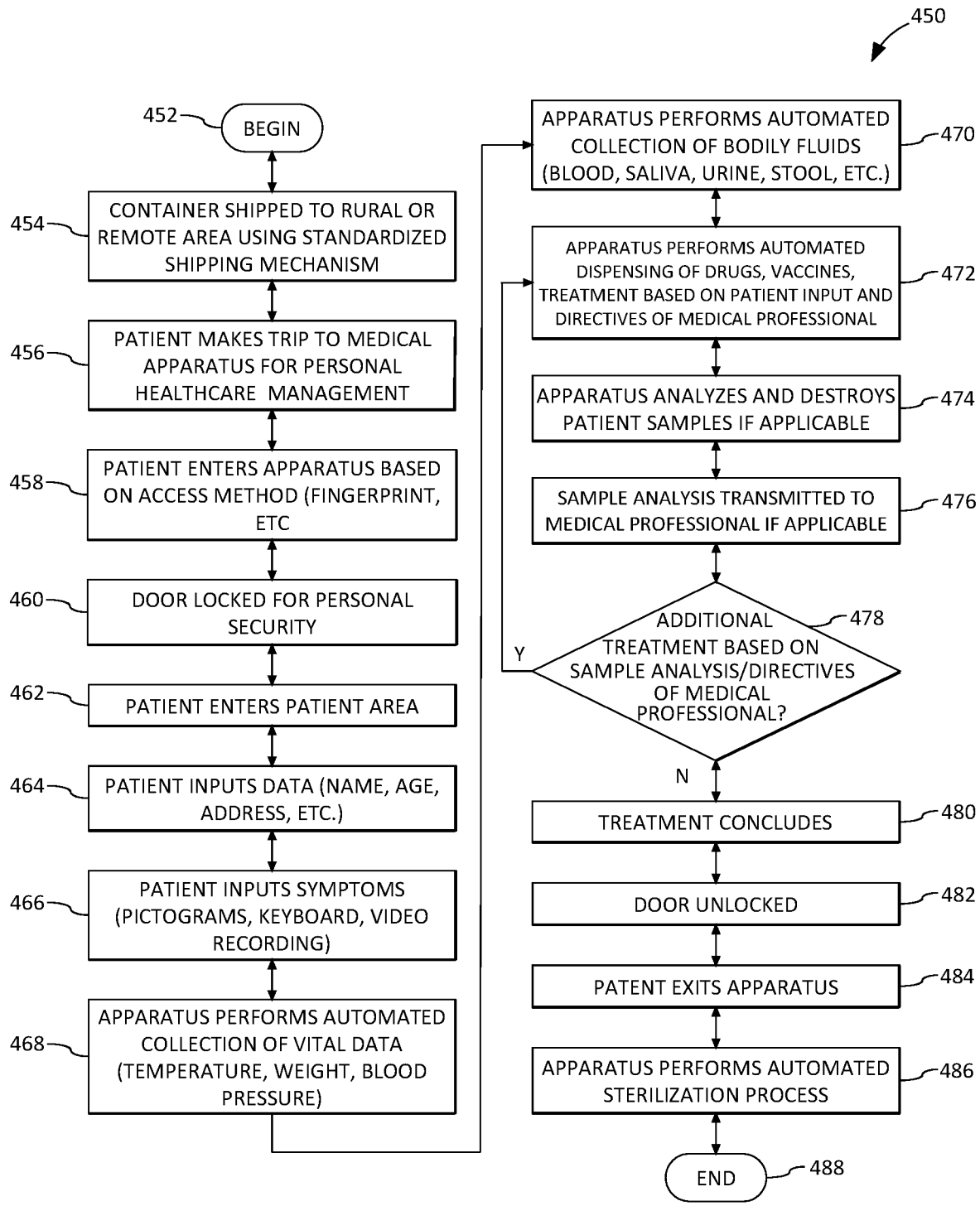
FIG. 13 illustrates an exemplary method of operation of the apparatus illustrated in FIG. 2.
Figure 14:
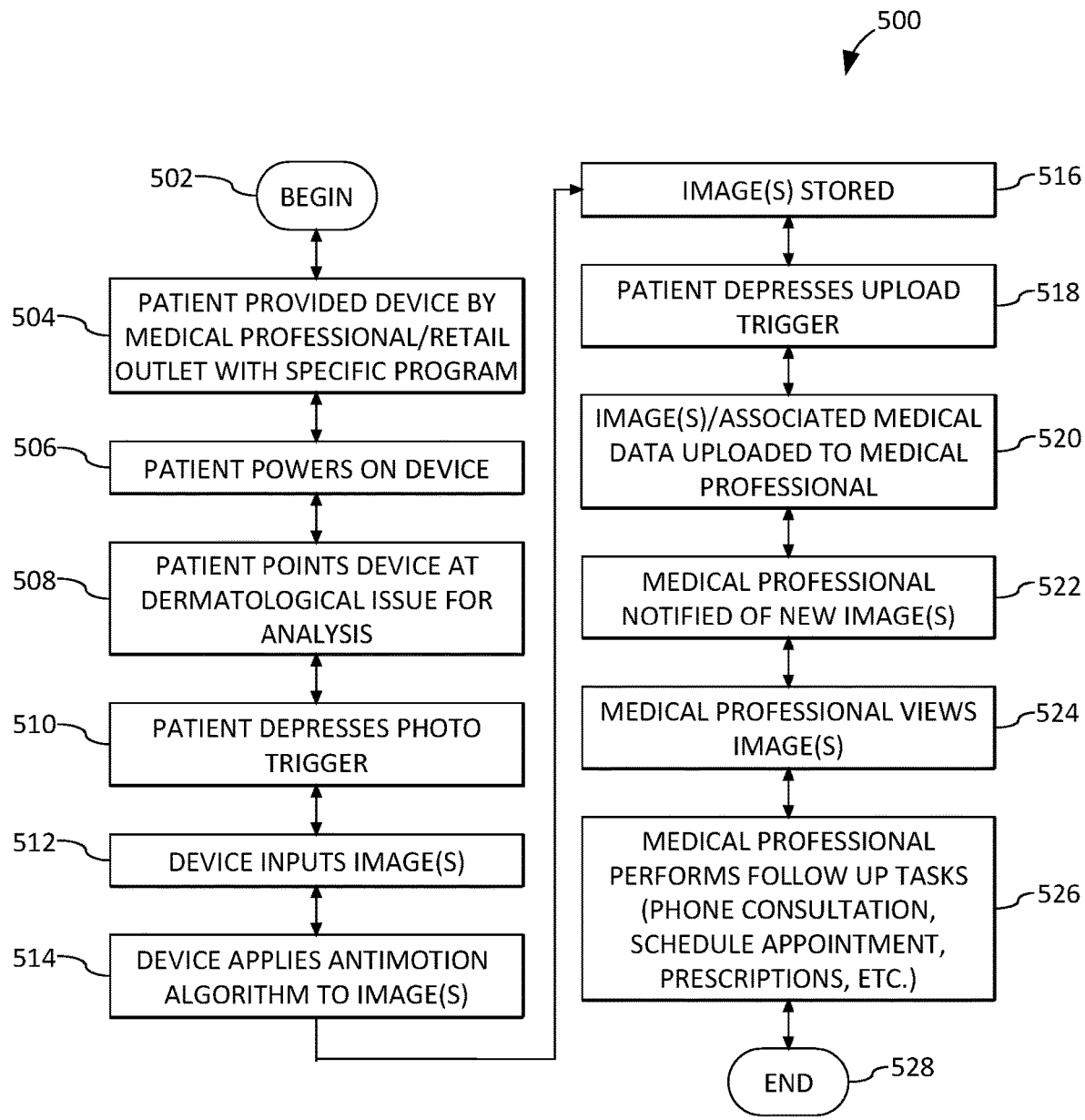
FIG. 14 illustrates an exemplary method of operation of the device illustrated in FIG. 6.
Figure 15:
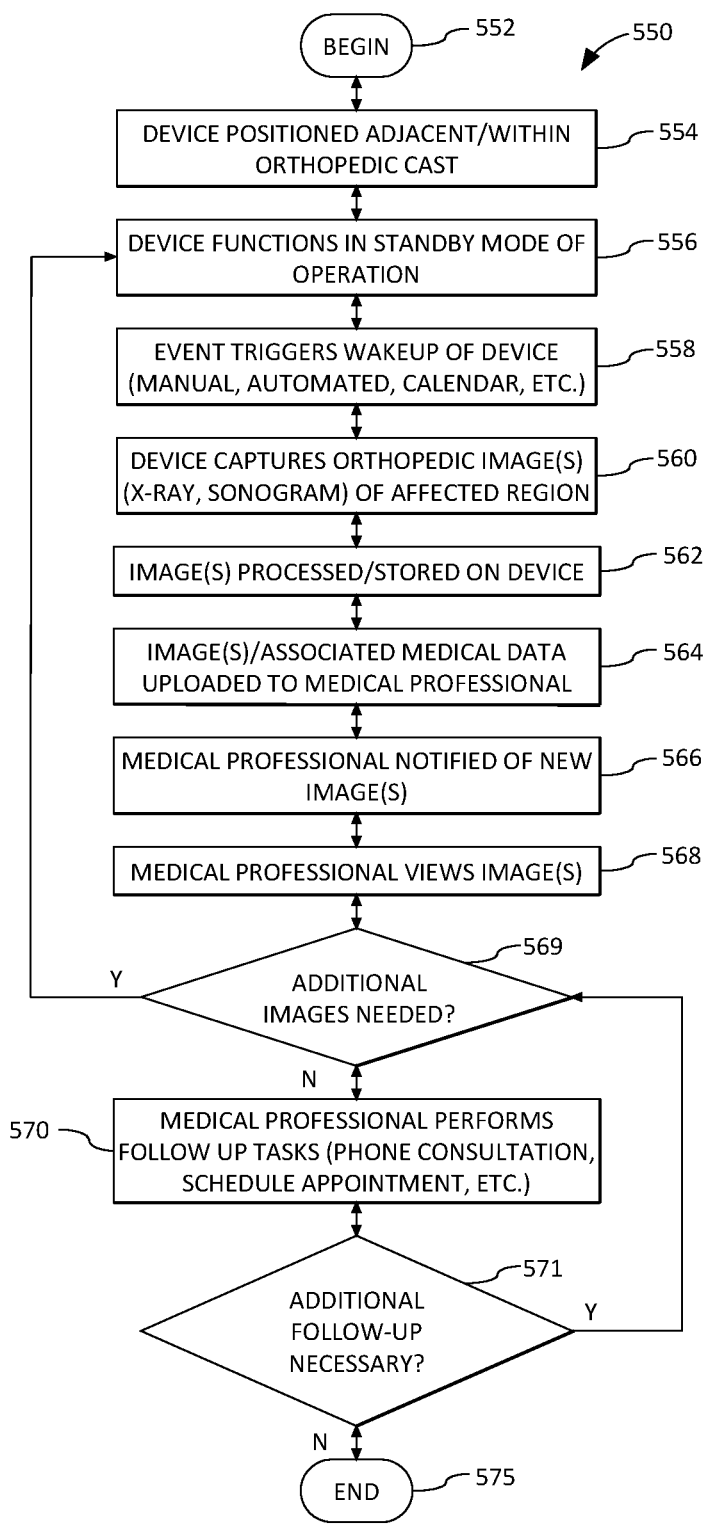
FIG. 15 illustrates an exemplary method of operation of the device illustrated in FIG. 10.

Turning to FIGS. 13-15, various methods are depicted, as examples of patient monitoring and treatment using the mechanisms of the present invention. As one skilled in the art will appreciate, various steps in these methods may be implemented in differing ways to suit a particular application. In addition, the described methods may be implemented by various means, such as hardware, software, firmware, or a combination thereof operational on or otherwise associated with the storage environment. For example, the methods may be implemented, partially or wholly, as a computer program product including a computer-readable storage medium having computer-readable program code portions stored therein. The computer-readable storage medium may include disk drives, flash memory, digital versatile disks (DVDs), compact disks (CDs), and other types of storage mediums.

Turning first to FIG. 13, method 450 illustrates an exemplary method of operation of the medical apparatus depicted in FIG. 2. Method 450 begins (step 452) with the shipment or placement of the container to a rural or remote area using a standardized shipping mechanism (step 454). The patient makes a trip to the medical apparatus for personal healthcare management (step 456). The patient enters the apparatus based on a particular access method (fingerprint, key, voice recognition, etc.) (step 458). The door is then locked for personal security (step 460).

The patient enters the patient area (step 462) and provides patient input (such as name, age, address, etc.) (step 464). The patient inputs symptoms (such as by use of pictograms, keyboard, video recording, etc.) (step 466). The apparatus then performs automated collection of vital data (such as temperature, weight, and blood pressure) (step 468). The apparatus then performs automated collection of bodily fluids (such as blood, saliva, urine, stool, etc.) (step 470). Based on the patient input and/or a preliminary analysis of the sample(s), and under the direction of the medical professional, the apparatus then performs automated dispensing of drugs, vaccines, and other treatment (step 472).

The analysis of the patient sample may continue (for example, if a culture is required) for some time, perhaps following exit of the patient from the apparatus. Once the sample is finished undergoing analysis, it is destroyed (step 474), and the analysis is transmitted to the medical professional (step 476). If additional treatment based on a sample analysis and/or the directives of the medical professional is needed (step 478), then steps 472-478 continue until treatment concludes (step 480). The door is unlocked (step 482), the patient exits apparatus (step 484), and the apparatus performs an automated sterilization process (step 486). The method 450 then ends (step 488).

Turning now to FIG. 14, an exemplary method 500 for operation of the device 258 (FIG. 6) is illustrated. Method 500 begins (step 502) with the providing of the device by a medical professional or retail outlet. The device is programmed with a specific program (step 504) for collecting dermatological images. As a next step, the patient powers on the device (step 506), the patient aims the device at a dermatological issue for analysis (step 508), and depresses the photo button to obtain one or more dermatological images (step 510). The device inputs the images (step 512), and applies an anti-motion algorithm to improve image quality (step 514). The images are stored (step 516) on onboard memory.

The patient then depresses the upload button (step 518) to upload the dermatological information. The images and associated dermatological data (such as imaging device number, patient information, time of day, date, etc.) is uploaded to the medical professional (step 520). The medical professional is notified of the new images (step 522). The medical professional views and analyzes the images (step 524), and then performs follow-up tasks based on the analysis (step 526), such as performing phone consultations, scheduling a follow-up appointment, writing a prescription, etc. The method 500 then ends (step 528).

Turning now to FIG. 15, an exemplary method 550 for operation of the device 356 is illustrated. Method 550 begins (step 552) with the positioning of the device either adjacent to, or within, an orthopedic cast (step 554). The device functions in a standby mode of operation (step 556) until an event triggers the device to awake (step 558), such as a manual wakeup, an automated trigger, a calendared event, and the like.

Once the device is made active, one or more orthopedic images (e.g., x-ray, sonogram) are captured (step 560). The images are processed and stored on the device (step 562), and later uploaded to the medical professional along with the associated medical data in similar fashion to that previously described in FIG. 14 (step 564). The medical professional is notified of the new images (step 566). The medical professional views and analyzes the images (step 568).

In some cases, additional orthopedic images need to be obtained during the course of a patient's healing process. If additional images need be obtained (such as due to the course of an estimated healing period still underway) (step 569), then the method 500 returns to step 556 in a standby mode of operation until the next event triggers the wakeup of the device (again, step 558). Steps 560-568 continue again as previously described.

Following the conclusion of obtaining all scheduled images, uploading the images to the medical professional, and analysis by the medical professional, the professional performs follow-up tasks based on the analysis (step 570), such as performing phone consultations, scheduling a follow-up appointment, writing a prescription, etc. If additional follow-up treatment is necessary (step 571), then the method 550 queries again whether additional images need be taken (again, step 569). If yes, then the images are scheduled and obtained as before (returning to step 556). Additional follow-up tasks are again performed (again, step 570). If no additional follow-up is necessary (again, step 571), then the method 550 ends (step 572).

While the foregoing methods 450, 500, and 550 provide exemplary functionality of the mechanisms of the present invention, the skilled artisan will appreciate that similar functionality may be carried out. For example, in additional embodiments, the apparatus 100 (FIG. 2) may be adapted to contact emergency medical personnel in case of a medical emergency, such as a paramedic team or hospital emergency room. For example, if a patient provides diagnostic information indicating a medical emergency, appropriate responding personnel may be contacted. The diagnostic information may be electronically forwarded to the responding personnel for analysis.

Some of the functional units described in this specification have been labeled as modules in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices, or the like.

Modules may also be implemented in software for execution by various types of processors. An identified module of executable code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, as electronic signals on a system or network.

While one or more embodiments of the present invention have been illustrated in detail, the skilled artisan will appreciate that modifications and adaptations to those embodiments may be made without departing from the scope of the present invention as set forth in the following claims.

What is claimed is:

1. A portable apparatus for orthopedic monitoring of a patient, comprising:
   a housing positioned within an orthopedic cast such that at least a portion of the housing is disposed between the orthopedic cast and skin of the patient;
   a reusable diagnostic biomedical device integrated into the housing, wherein the diagnostic biomedical device is an ultrasonography imaging device adapted for obtaining an orthopedic image of a fractured bone portion of the patient treated with the orthopedic cast;
   wherein the ultrasonography imaging device includes an acoustic transducer positioned adjacent to the skin and disposed beneath the orthopedic cast for sending and receiving pulses of sound, an impedance-matching material positioned between the acoustic transducer and the housing, and a processor device contained within the housing and disposed beneath the orthopedic cast for interpreting received pulses of sound and generating the orthopedic image; and wherein the diagnostic biomedical device is programmed to automatically obtain additional orthopedic images of the fractured bone portion of the patient at predetermined intervals over a predetermined timeframe, the diagnostic biomedical device placed into a lowered power sleep mode of operation between the predetermined intervals;

a memory device in communication with the diagnostic biomedical device, wherein the memory device is adapted for storing the orthopedic image; and a wireless communications interface coupled to the diagnostic biomedical device, wherein the wireless communications interface is adapted to upload the orthopedic image to a remote server to be viewed by a medical professional; and wherein the housing further includes:

a first indicator light activated upon each successful capture of the orthopedic image, and a second indicator light activated upon a successful upload of the orthopedic image using the wireless communications interface to the remote server, wherein upon the successful upload, the orthopedic image is automatically deleted from the memory device.

2. The portable apparatus of claim 1, further including a power system integrated into the housing and in communication with the diagnostic biomedical device, wherein the power system is adapted for providing electrical power to at least one of the diagnostic biomedical device and the wireless communications interface.

3. The portable apparatus of claim 2, wherein the power system includes a battery device, the battery device accessible through the housing, wherein the battery device includes an indicator light for indicating a battery status.

4. The portable apparatus of claim 1, wherein the wireless communications interface is compatible with an Institute of Electrical and Electronics Engineers (IEEE) communications protocol.

* * * * *